United States Patent [19]

Krzysik et al.

[11] Patent Number: 5,160,494

[45] Date of Patent: Nov. 3, 1992

[54] ALKYLMETHYLSILOXANE CONTAINING PERFUME COMPOSITIONS

[75] Inventors: Duane G. Krzysik; Gary E. LeGrow, both of Midland, Mich.

[73] Assignee: Dow Corning Corporation, Midland, Mich.

[21] Appl. No.: 868,142

[22] Filed: Apr. 14, 1992

[51] Int. Cl.$^5$ .............................................. A61K 7/46
[52] U.S. Cl. .............................................. 512/3; 512/2
[58] Field of Search .................... 512/1, 2, 3; 556/456

[56] References Cited

U.S. PATENT DOCUMENTS

| | | | |
|---|---|---|---|
| 2,469,888 | 5/1949 | Patnode | 556/457 |
| 3,767,787 | 10/1973 | Segal | 512/2 |
| 4,631,273 | 12/1986 | Blehm et al. | 512/1 |
| 5,079,227 | 1/1992 | Handjani et al. | 512/2 |
| 5,081,104 | 1/1992 | Orson | 512/3 |

Primary Examiner—James H. Reamer
Attorney, Agent, or Firm—Jim L. DeCesare

[57] ABSTRACT

A composition which is an emulsifier-free mixture of a perfume oil and a cyclic alkylmethylsiloxane having the formula

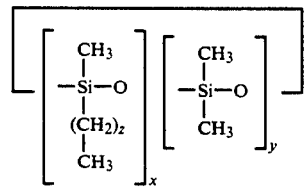

in which x and y are each integers and the sum of x and y is four, five or six with the proviso that x and y cannot be zero; and z is an integer having a value of 5-50.

10 Claims, No Drawings

ALKYLMETHYLSILOXANE CONTAINING PERFUME COMPOSITIONS

BACKGROUND OF THE INVENTION

This invention relates to an improvement in perfumes and more particularly to an improvement in concentrated alcoholic solutions of perfume oils used by consumers to impart a fragrance. The improvement resides in the substitution of certain organosilicon compounds for the alcohol component of the perfume.

Perfume oils may be categorized as (i) plant materials such as essential oils obtained by distillation or expression; flower oils obtained by extraction; resins, gums, and exudations such as myrrh, benzoin, labdanum, and gum styrax; (ii) animal secretions such as castoreum, civet, musk, and ambergris; and (iii) chemical substances including isolates from plant materials such as eugenol, citral, and geraniol; derivatives of plant materials such as linalyl acetate, geranyl acetate, and hydroxycitronellal; and synthetic organic substances such as benzyl acetate, mush ambrette, and amyl cinnamic aldehyde. The important types of fragrance produced by such perfume oils include oriental, cologne blend, bouquet, floral, chypre, fougere, spice blend, wood blend, aldehydic blend, and amber.

The most popular product on the market for imparting a fragrance is in the form of an alcoholic solution of the perfume oil. Such products may be marketed under the names perfume, toilet water, eau de toilette, cologne, eau de cologne, eau de parfum, essence, or fragrant water. Typically, these products contain a certain percentage of the perfume oil in 95 percent denatured ethyl alcohol which includes only a very small percentage of water.

However, because of recent federal and state legislation aimed at lowering air pollution, a need has been created for consumer products which contain limited amounts of organic solvents. These air pollution regulations limit the amount of organic solvents that can be discharged into the atmosphere. The term used for solvents is "volatile organic compounds" (VOC). A volatile organic compound (VOC) is defined as any compound of carbon that has a vapor pressure greater than 0.1 millimeter of mercury at a temperature of twenty degrees Centigrade and a pressure of 760 millimeters mercury.

"Volatile organic content" has been defined as the amount of volatile organic compounds (VOC) liberated from a coating as determined by ASTM D3690 and EPA Reference Method 24 which are standard industrial tests. Under the definition, a volatile organic compound is any compound which enters the atmosphere and photochemically reacts in the atmosphere with nitrogen oxides to reduce ozone and form photochemical smog.

Reduction of VOC has been mandated in several states and regulations in California for example require less than about four hundred grams of volatiles per liter of product to enter the atmosphere. This can be determined by baking ten grams of a product in an oven at one hundred-ten degrees Centigrade for one hour. The amount of solids which remain is subtracted from the total of the ten grams which was tested. Calculations are based on the weight of the volatiles that have evaporated which is reported as grams per liter.

The federal Environmental Protection Agency (EPA) has identified many volatile organic compounds present in consumer products such as the more common solvents ethanol, isopropyl alcohol, kerosene, and propylene glycol, in addition to hydrocarbon solvents such as isobutane, butane, and propane which are employed as propellants in consumer products.

Some states have proposed standards which would limit and reduce the amount of volatile organic compounds (VOC) permitted in various consumer products such as chemically formulated products used by household and institutional consumers including detergents; cleaning compounds; polishes; floor products; cosmetics; personal care products; home, lawn and garden products; disinfectants; sanitizers; and automotive specialty products. These standards would effect such widely used consumer products as shaving lather, hairspray, shampoos, colognes, perfumes, aftershave, deocolognes, pre-electric shaves, deodorants, antiperspirants, suntan preparations, lotions, breath fresheners, and room deodorants.

Thus, the need for new and novel formulations and techniques for reducing organic emissions should be more than apparent. In accordance with the present invention, it has been discovered that certain organosilicon compounds meet this need.

SUMMARY OF THE INVENTION

The invention is directed to a perfume composition for imparting a fragrance which is in the form of a mixture of a perfume oil and a volatile short chain linear alkylmethylsiloxane or a volatile cyclic alkylmethylsiloxane. The function of the alkylmethylsiloxane is to act as a substitute for ethanol in compositions previously known as alcoholic fragrance solutions.

It is an object of the present invention to provide a perfume composition containing a volatile alkylmethylsiloxane as a delivery vehicle for a perfume oil.

It is another object of the present invention to provide a perfume composition containing a delivery vehicle for a perfume oil which has good compatibility with the perfume oil, nonirritating and nonstinging to the skin, and which has a low heat of evaporation so as to be noncooling to the skin.

The volatile alkylmethylsiloxanes of the present invention fulfill the foregoing objectives. Because of the presence in the molecule of long chain alkyl groups, the volatile alkylmethylsiloxanes possess enhanced compatibility with organic materials such as a perfume oil. As a substitute for all or a portion of the ethanol in alcoholic fragrance solutions, the volatile alkylmethylsiloxanes of the present invention have the additional advantage of eliminating the disadvantages associated with ethanol based products such as a stinging effect on abraded skin, a cooling sensation because of the high heat of evaporation of ethanol, the flammability of ethanol, and the environmental concerns of ethanol noted previously.

The perfume compositions of the present invention are emulsifier-free and hence even less irritating to the skin. Some perfume compositions contain emulsifying solubilizing agents which have been determined to be potential skin irritants. Of the numerous problems faced by perfume formulators, none is quite as important as the elimination of any tendency of the perfume to cause irritation, sensitization, or sensitizing synergisms. Therefore and in accordance with the present invention, the perfume compositions are preferably emulsifier-free thereby avoiding many of the disadvantages associated with prior art compositions which include potentially skin irritating emulsifying agents. Thus, the present invention is not intended to cover perfume compositions in the form of an emulsion and which may be variously known as cream sachets, liquid sachets, lotion sachets, liquid skin sachets, liquid cream sachets, cream lotion sachets, perfume cream sachets, veils of perfume, silks, or skin balms.

In the most preferred embodiment of the present invention, the perfume composition is anhydrous. In this embodiment, a perfume oil is combined with a volatile alkylmethylsiloxane. If it is desired to include a small portion of ethanol, the ethanol is preferably anhydrous ethanol. These anhydrous emulsifier-free perfume compositions have improved clarity, and the solubility and compatibility of the ingredients is improved, by avoiding the inclusion of water.

The perfume compositions of the present invention may be applied in the same fashion as conventional perfumes and colognes. Thus, the compositions are applied as a dab behind each ear, on the wrists, temple, at the crook of the elbow, between the breasts, or behind the knees.

These and other features, objects, and advantages of the herein described present invention will become more apparent from a consideration of the following detailed description thereof.

DETAILED DESCRIPTION OF THE INVENTION

Perfume oils suitable for use in the perfume compositions of the present invention may include any type of material which may be classified as a fragrance, cologne, or perfume. For example, the perfume oil may be a natural product such as ambergris, benzoin, civet, clove, leaf oil, galbanum, jasmine, absolute labdanum, mate', melilot, mimosa, musk, tonquin, myrrh, mousse de chene, olibanum, opopanax, orris, patchouli, rosemary oil, sandalwood oil, vetivert oil, and violet leaves absolute. Among the various aroma chemicals that may be employed as the perfume oil in addition to the foregoing natural products are acetylated cedarwood terpenes, amyl cinnamic aldehyde, amyl salicylate, methyl salicylate, benzyl acetate, benzyl salicylate, p--tert-butyl cyclohexyl acetate, citronellol, coumarin, galaxolide, geraniol, hexyl cinnamic aldehyde, isobornyl acetate, linalool, linalyl acetate, lyral, ambrette, phenethyl alcohol, tetrahydromuguol, and terpinyl acetate. Fragrances that have become classics as descriptors for other perfume oils in the same family are also included herein and would comprehend perfume oils in the straight floral family, the floral bouquet family, the aldehydic floral family, the oriental family, the chypre family, the woody family, the green family, the citrus family, the fougere family, the canoe family, the musk family, the animal family, the leather family, the spice family, and the herbal family.

While the primary ingredients of the perfume compositions of the present invention are the perfume oil and the volatile alkylmethylsiloxane, the compositions may optionally include other minor amounts of ingredients necessary to provide a more acceptable consumer oriented product. Thus, a coloring agent may be required such as D & C Red No. 19, D & C Green No. 5, and FD & C Yellow No. 5, which are CTFA adopted names of The Cosmetic, Toiletry, and Fragrance Association, Inc., Washington, D.C. In some instances, a preservative may be required such as methyl paraben, phenoxyethanol, diazolidinyl urea, and 5-chloro-2-methyl-4-isothiazolin-3-one. Where an antimicrobial agent is required, materials such as Triclosan, Quaternium-15, chloroxylenol, and cetyl trimethyl ammonium bromide may be employed. Aerosol delivery of the perfume compositions of the invention will require a propellant including volatile hydrocarbons such as isobutane or propane; dimethylether; carbon dioxide; nitrogen; or nitrous oxide; where an aerosol is a desirable mode of delivery. Antioxidants such as natural mixed tocopherols may also be employed.

For economic reasons, it may be necessary to use the volatile short chain linear alkylmethylsiloxane or the volatile cyclic alkylmethylsiloxane in combination with another volatile silicone. In those instances, the volatile silicone is a methylsilicone fluid corresponding to the average unit formula $(CH_3)_aSiO_{(4-a/2)}$ wherein a is an integer having an average value of from two to three. The methylsiloxane fluid includes siloxane units joined by Si-O-Si bonds. Respresentative units are $(CH_3)_3SiO_{1/2}$, $(CH_3)_2SiO_{2/2}$, $(CH_3)SiO_{3/2}$, and $SiO_{4/2}$. These units are present in such molar amounts so that there is an average of from about two to three methyl groups per silicon atom in the methylsiloxane fluid, and the fluid has a viscosity of less than about one hundred centistokes measured at twenty-five degrees Centigrade.

Preferably, the methylsiloxane fluid contains dimethylsiloxane units and optionally trimethylsiloxane units. Of particular utility are methylsiloxane fluids having a viscosity of less than about ten centistokes such as cyclopolysiloxanes of the general formula $[(CH_3)_2SiO]_x$ and linear siloxanes of the general formula $(CH_3)_3SiO[(CH_3)_2SiO]_ySi(CH_3)_3$ in which x is an integer having a value of from three to ten and y is an integer having a value of from zero to about four. Some representative volatile cyclic methylsiloxane compounds are the methylsiloxane tetramer octamethylcyclotetrasiloxane and the methylsiloxane pentamer decamethylcyclopentasiloxane, Mixtures of the tetramer and pentamer may also be employed. Such cyclic siloxanes have viscosities ranging from about 2.5 centistokes to about five centistokes. Of the linear siloxanes, hexamethyldisiloxane which has a viscosity of 0.65 centistokes is preferred. The cyclic methylsiloxanes materials are known under the CTFA adopted name of The Cosmetics, Toiletries and Fragrance Association, Inc., Washington, D.C., as cyclomethicone. Both the cyclic and linear low viscosity volatile methylsiloxane materials are clear fluids and are essentially odorless, nontoxic, nongreasy and nonstinging. Cosmetically these methylsiloxane fluids are nonirritating to the skin and exhibit enhanced spreadability and ease of rub-out when applied to skin tissue. Once applied, the materials will evaporate leaving behind no residue. Thus, they possess enhanced compatibility with the volatile short chain linear alkylmethylsiloxane and the volatile cyclic alkylmethylsiloxanes of the present invention.

If it is desired to include a minor amount of some additional materials for the purpose of facilitating the emolliency characteristics of the perfume compositions of the invention, some appropriate materials are straight, branched or cyclic hydroxy compounds such as alcohols containing 1-30 carbon atoms; straight, branched or cyclic carboxylic acids containing 1-30 carbon atoms; acid esters containing C1 to C30 caboxylic acids esterified with C1 to C30 alcohols; alcohol ethers containing 1-30 carbon atoms; and alkanes of the formula H—(CH$_2$)$_n$—H where n is 5-30. Specific examples of some of these materials are 2-ethylhexyl oxystearate; arachidyl propionate; 2-ethylhexyl adipate; isopropyl myristate; stearyl alcohol; propionic acid; stearic acid; mineral oil; aliphatic hydrocarbons such as mineral spirits; and lanolin and lanolin derivatives such as acetylated lanolin and isopropyl lanolate. Humectants such as glycerin may also be employed.

The perfume composition in accordance with the present invention is an anhydrous emulsifier-free mixture of a perfume oil and a volatile short chain alkylmethylsiloxane or a volatile cyclic alkylmethylsiloxane having the formulas

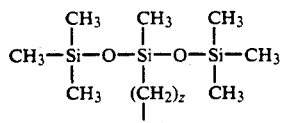

and

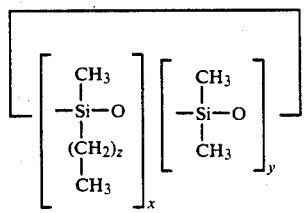

in which the sum of the integers x and y is four, five or six, with the proviso that x and y cannot be zero; and z is an integer having a value of 1-12. Preferably, z is six, seven, or eight. Other preferred cyclic alkylmethylsiloxanes of the invention are represented by the formula shown above and wherein (i) x is one and y is three, four or five; (ii) x is two, and y is two, three or four; (iii) x is three, and y is one, two or three; (iv) x is four, and y is one or two; and (v) x is five, and y is one. In each of the preferred modes (i)-(v), z is 1-12 preferably 6-8 as indicated above.

The volatile short chain alkylmethylsiloxane and the volatile cyclic alkylmethylsiloxane shown above are known in the art and are commercially available. Methods of preparing such materials are also well known in the art. In any event, the preparation of such materials is described below.

The alkylmethyl polysiloxanes of this invention can be produced by the reaction of a linear siloxane having Si—H functionality in the chain such as (Me$_3$SiO$_\frac{1}{2}$)$_2$(OSiMeH)$_x$ in which Me is methyl and x is forty to about one hundred, and a cyclic siloxane having (Me$_2$SiO) units of the formula (Me$_2$SiO)$_x$ in which Me is methyl and x is an integer of about three to six preferably four or five. The reaction product is then contacted with a slight stoichiometric excess of an alkene CH$_2$=CHR in the presence of a platinum on carbon catalyst and an alkylmethylsiloxane having the structure shown above is produced.

The alkylmethyl polysiloxanes of this invention can also be produced by the direct hydrolysis of methylhydrogen dichlorosilane to form cyclomethylhydrogen polysiloxanes, or by the direct cohydrolysis of methylhydrogen dichlorosilane and dimethyl dichlorosilane to form cyclomethylhydrogensiloxy dimethylsiloxy copolymers. The reaction product is then contacted with a slight stoichiometric excess of an alkene CH$_2$=CHR in the presence of a platinum on carbon catalyst and an alkylmethylsiloxane having the structure shown above is produced.

Batch production of the alkylmethyl polysiloxanes is conducted by adding the reaction product to a non-agitated suspension of the catalyst in the alkene at about sixty degrees Centigrade. Continuous production of the alkylmethyl polysiloxanes is conducted by pumping a preheated solution of a five percent stoichiometric excess of an alkene CH$_2$=CHR and the reaction product through a packed column containing platinum on carbon catalyst chips. The column will require provision for the removal of heat because of the exothermic nature of the reaction.

The materials are further processed in accordance with the present invention in order to provide a more cosmetically acceptable product by removing from the product any remaining cyclic siloxane and any residual methylhydrogendimethylsiloxane cocyclics present as (MeHSiO)(Me$_2$SiO)$_3$. The alkylmethyl polysiloxanes produced in accordance with the present invention have been found to contain at most about 0.5 percent residual alkene and about 99.5 percent alkylmethyl polysiloxane product. No measurable residual amount of platinum has been detected. The products are otherwise colorless, odorless, clear and stable materials. The products are particularly adapted to skin care in that the materials have been found to form films on the skin which possess a very low water vapor permeability enabling the materials to form a barrier on the skin which will reduce moisture loss from the stratum corneum.

The following examples illustrate the method of making cyclic alkylmethylsiloxanes.

EXAMPLE I

A suspension of 1.2 grams of 0.5% Pt/C in 120 grams of dry hexene-1 was stirred and heated to reflux. To this suspension was slowly added 80 grams of (MeHSiO)$_4$. After complete addition, the mixture was heated at 100° C. for 1 hour, then cooled and filtered to remove the Pt/C catalyst. The mixture was then heated and evacuated, removing 10 grams of excess hexene-1. The remaining material was distilled to produce 185 grams (95%) of (C$_6$H$_{13}$MeSiO)$_4$, having a boiling point of 350° C., a refractive index of 1.4374, a density of 0.90 g/ml, and a viscosity of 14 cs.

EXAMPLE II

A suspension of 1.2 grams of 0.5% Pt/C in 80 grams of dry hexene-1 was stirred and heated to reflux. To this suspension was slowly added 120 grams of a mixture of cyclic (HMeSiO)$_x$(Me$_2$SiO)$_y$ having a boiling point of 145°-165° C., wherein x=1:y=3, x=2:y=2, and x=3:y=1. After complete addition, the mixture was heated to 100° C. for 1 hour, then cooled and filtered to remove the Pt/C catalyst. The mixture was heated and evacuated, removing 6 grams of excess hexene-1. The remaining 190 grams of material was a liquid mixture of cyclic (C$_6$H$_{13}$MeSiO)$_x$(Me$_2$SiO)$_y$, wherein x=1:y=3, x=2:y=2 and x=3:y=1 having a refractive index of 1.4170, a density of 0.93 g/ml, and a viscosity of 6 cs.

The perfume compositions of this invention contain 5-30 percent by weight of the perfume oil, and 1-95 percent by weight of the volatile alkylmethylsiloxane. Preferable amounts are 5-20 percent by weight of the perfume oil, and 5-50 percent by weight of the volatile alkylmethylsiloxane. In addition to the perfume oil and the alkylmethylsiloxane, the perfume composition optionally may include 0-90 percent by weight of anhydrous ethanol, preferably 40-90 percent by weight; 0-40 percent by weight of a volatile methylsilicone fluid, preferably 5-20 percent by weight; 0-5 percent by weight of an emollient or a humectant, preferably about two percent by weight; and 0-1 percent by weight of each of a preservative, a colorant, an antimicrobial agent, or an antioxidant, as needed. The compositions are particularly suitable for use as perfumes, colognes, after shaves, deo-colognes, and pre-electric shaves.

The following additional example illustrates the preparation of perfume compositions in accordance with the present invention.

EXAMPLE III

Some eleven (11) perfume compositions were prepared including four (4) perfumes, three (3) colognes, three (3) after shaves, and one (1) pre-electric shave. These compositions were prepared by mixing together the various ingredients in the amounts shown below in the Tables. The ingredients were mixed together in the order in which they are listed in the Tables. All of the formulations were clear except for Perfume "G" which exhibited a slight haze. The fragrance oils are products of Noville Corporation, North Bergen N.J. The ethanol employed was anhydrous 200 proof ethanol. The alkylmethylsiloxane shown in the Tables corresponds to the volatile short chain linear alkylmethylsiloxane shown in the previous formula in which z is six. The volatile cyclic methylsilicone fluid employed was decamethylcyclopentasiloxane. The volatile linear methylsilicone fluid was hexamethyldisiloxane. All amounts shown in the Tables are weight percent.

TABLE I

| Ingredient | Perfume A | Cologne B | Perfume C |
|---|---|---|---|
| Fragrance Oil | | | |
| Eternity Type I | 15.0 | 7.5 | — |
| Obsession Type | — | — | 15.0 |
| Trouble Type | — | — | — |
| Cool Water Type | — | — | — |
| Fahrenheit Type | — | — | — |
| Eternity Type II | — | — | — |
| Ethanol (200 proof) | 45.0 | 72.5 | 40.0 |
| Alkylmethyl Siloxane | 40.0 | 20.0 | 45.0 |
| Volatile Cyclic Methylsilicone | — | — | — |
| Volatile Linear Methylsilicone | — | — | — |
| Glycerin | — | — | — |

TABLE II

| Ingredient | Cologne D | Cologne E | Perfume F |
|---|---|---|---|
| Fragrance Oil | | | |
| Eternity Type I | — | — | — |
| Obsession Type | 7.5 | 7.5 | — |
| Trouble Type | — | — | 15.0 |
| Cool Water Type | — | — | — |
| Fahrenheit Type | — | — | — |
| Eternity Type II | — | — | — |
| Ethanol (200 proof) | 49.5 | 49.5 | 45.0 |
| Alkylmethyl Siloxane | 23.0 | 23.0 | 40.0 |
| Volatile Cyclic Methylsilicone | 20.0 | — | — |
| Volatile Linear Methylsilicone | — | 20.0 | — |
| Glycerin | — | — | — |

TABLE III

| Ingredient | Perfume G | Pre-Electric Shave H | After Shave I |
|---|---|---|---|
| Fragrance Oil | | | |
| Eternity Type I | — | — | — |
| Obsession Type | — | — | — |
| Trouble Type | 15.0 | — | — |
| Cool Water Type | — | 6.0 | — |
| Fahrenheit Type | — | — | 6.0 |
| Eternity Type II | — | — | — |
| Ethanol (200 proof) | — | 89.0 | 79.0 |
| Alkylmethyl Siloxane | 85.0 | 5.0 | 15.0 |
| Volatile Cyclic Methylsilicone | — | — | — |
| Volatile Linear Methylsilicone | — | — | — |
| Glycerin | — | — | — |

TABLE IV

| Ingredient | After Shave J | After Shave K |
|---|---|---|
| Fragrance Oil | | |
| Eternity Type I | — | — |
| Obsession Type | — | — |
| Trouble Type | — | — |
| Cool Water Type | — | — |
| Fahrenheit Type | — | — |
| Eternity Type II | 6.0 | 6.0 |
| Ethanol (200 proof) | 72.0 | 72.0 |
| Alkylmethyl Siloxane | 15.0 | 15.0 |
| Volatile Cyclic Methylsilicone | 5.0 | — |
| Volatile Linear Methylsilicone | — | 5.0 |
| Glycerin | 2.0 | 2.0 |

It will be apparent from the foregoing that many other variations and modifications may be made in the compounds, compositions, structures, and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A composition comprising an anhydrous emulsifier-free mixture of a perfume oil and an alkylmethylsiloxane having a formula selected from the group consisting of

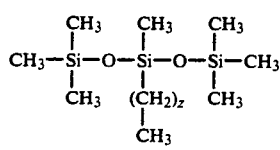

and

-continued

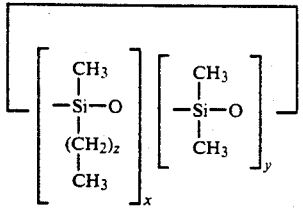

in which the sum of the integers x and y is four, five or six with the proviso that x and y cannot be zero; and z is an integer having a value of 1-12.

2. The composition of claim 1 in which x is one, y is three, four or five, and z is 6-8.

3. The composition of claim 1 in which x is two, y is two, three or four, and z is 6-8.

4. The composition of claim 1 in which x is three, y is one, two or three, and z is 6-8.

5. The composition of claim 1 in which x is four, y is one or two, and z is 6-8.

6. The composition of claim 1 in which x is five, y is one, and z is 6-8.

7. The composition of claim 1 in which the mixture includes anhydrous ethanol.

8. The composition of claim 1 in which the mixture includes 5-30 percent by weight of the perfume oil, and 1-95 percent by weight of the alkylmethylsiloxane.

9. The composition of claim 1 in which the mixture includes 5-20 percent by weight of the perfume oil, 5-50 percent by weight of the alkylmethylsiloxane, 40-90 percent by weight of anhydrous ethanol, 5-20 percent by weight of a methylsilicone fluid, and a humectant.

10. The composition of claim 9 in which the methylsilicone fluid is selected from the group consisting of decamethylcyclopentasiloxane and hexamethyldisiloxane, and the humectant is glycerin.

* * * * *